US011344486B2

(12) United States Patent
Qiao et al.

(10) Patent No.: US 11,344,486 B2
(45) Date of Patent: *May 31, 2022

(54) ZINC PHOSPHATE COMPLEX

(71) Applicant: Colgate-Palmolive Company, New York, NY (US)

(72) Inventors: Baohua Qiao, Howell, NJ (US); Long Pan, Somerset, NJ (US); Gregory Szewczyk, Flemington, NJ (US); Ravi Subramanyam, Belle Mead, NJ (US); Shiri Nawrocki, Tenafly, NJ (US); Viktor Dubovoy, Cresskill, NJ (US)

(73) Assignee: Colgate-Palmolive Company, New York, NY (US)

( * ) Notice: Subject to any disclaimer, the term of this patent is extended or adjusted under 35 U.S.C. 154(b) by 136 days.

This patent is subject to a terminal disclaimer.

(21) Appl. No.: 16/425,122

(22) Filed: May 29, 2019

(65) Prior Publication Data

US 2019/0274936 A1 Sep. 12, 2019

Related U.S. Application Data

(63) Continuation of application No. 15/539,275, filed as application No. PCT/US2014/072421 on Dec. 26, 2014, now Pat. No. 10,350,151.

(51) Int. Cl.
| | | |
|---|---|---|
| *A61K 8/27* | (2006.01) | |
| *A61K 8/24* | (2006.01) | |
| *A61Q 15/00* | (2006.01) | |
| *A61Q 11/00* | (2006.01) | |
| *A61K 33/30* | (2006.01) | |
| *A61K 33/42* | (2006.01) | |

(52) U.S. Cl.
CPC ............... *A61K 8/27* (2013.01); *A61K 8/24* (2013.01); *A61Q 11/00* (2013.01); *A61Q 15/00* (2013.01)

(58) Field of Classification Search
CPC . A61K 8/27; A61K 8/24; A61K 33/30; A61K 33/42; A61Q 11/00; A61Q 15/00; C07F 3/003
See application file for complete search history.

(56) References Cited

U.S. PATENT DOCUMENTS

| | | | |
|---|---|---|---|
| 4,645,662 A | 2/1987 | Nakashima et al. | |
| 4,663,154 A * | 5/1987 | Ryan | A61K 8/4926 424/54 |
| 5,000,944 A * | 3/1991 | Prencipe | A61K 8/24 424/57 |
| 5,486,350 A | 1/1996 | Norfleet et al. | |
| 5,643,559 A | 7/1997 | Eigen et al. | |
| 6,015,547 A * | 1/2000 | Yam | A61K 8/19 424/462 |
| 8,906,347 B2 | 12/2014 | Strand et al. | |
| 9,005,586 B2 | 4/2015 | Prencipe | |
| 9,450,894 B2 | 9/2016 | Edmiston | |
| 9,498,421 B2 | 11/2016 | Liu et al. | |
| 9,504,858 B2 | 11/2016 | Yuan et al. | |
| 9,579,269 B2 | 2/2017 | Mello et al. | |
| 9,757,316 B2 | 9/2017 | Pan et al. | |
| 9,763,865 B2 | 9/2017 | Pan et al. | |
| 9,775,792 B2 | 10/2017 | Liu et al. | |
| 9,827,177 B2 | 11/2017 | Yuan et al. | |
| 9,901,523 B2 | 2/2018 | Xu et al. | |
| 9,925,130 B2 | 3/2018 | Pan et al. | |
| 9,980,890 B2 | 5/2018 | Pan et al. | |
| 2006/0099152 A1 ‡ | 5/2006 | Day | A61K 8/23 424/49 |
| 2007/0025928 A1 | 2/2007 | Glandorf et al. | |
| 2007/0183989 A1 | 8/2007 | Prencipe et al. | |
| 2011/0020247 A1 | 1/2011 | Strand | |
| 2013/0171224 A1* | 7/2013 | Percival | A61L 26/0004 424/404 |
| 2013/0230469 A1* | 9/2013 | Lewus | A61K 8/4913 424/52 |
| 2014/0086851 A1 | 3/2014 | Fisher et al. | |
| 2015/0297500 A1 | 10/2015 | Robinson et al. | |
| 2015/0305993 A1 | 10/2015 | Rege et al. | |
| 2015/0313813 A1 | 11/2015 | Rege et al. | |
| 2015/0328118 A1 | 11/2015 | Pan et al. | |
| 2017/0326046 A1 | 11/2017 | Pan | |
| 2017/0340534 A1 | 11/2017 | Nawrocki | |
| 2017/0348207 A1 | 12/2017 | Qiao | |
| 2017/0348352 A1 | 12/2017 | Qiao | |
| 2018/0008519 A1 | 1/2018 | Qiao | |

FOREIGN PATENT DOCUMENTS

| | | | |
|---|---|---|---|
| CA | 2663913 | | 4/2008 |
| CA | 2663913 A1 ‡ | | 4/2008 |
| CA | 2703078 | | 5/2009 |
| EP | 1633818 | | 3/2006 |
| EP | 2057978 | | 5/2009 |
| EP | 2068814 | | 6/2009 |
| EP | 2068814 A1 ‡ | | 6/2009 |
| EP | 2112882 | | 11/2009 |
| EP | 2246031 | | 11/2010 |
| EP | 2246031 A1 ‡ | | 11/2010 |
| WO | 1994/014406 | | 7/1994 |
| WO | WO 1994/014406 | ‡ | 7/1994 |
| WO | 2000/038644 | | 7/2000 |
| WO | 2001/039606 | | 6/2001 |
| WO | 2008/041055 | | 4/2008 |
| WO | 2008/089822 | | 7/2008 |
| WO | 2009/060385 | | 5/2009 |
| WO | 2010/019729 | | 2/2010 |
| WO | 2011/016984 | | 2/2011 |
| WO | 2013/013902 | | 1/2013 |

(Continued)

OTHER PUBLICATIONS

International Search Report and Written Opinion of the International Searching Authority in International Application No. PCT/US2014/072421, dated Jun. 25, 2015.‡

*Primary Examiner* — Monica A Shin

(57) ABSTRACT

A soluble zinc polyphosphate complex made by combining ingredients which include an organic zinc salt and a plurality of long chain polyphosphates having 6 or more phosphate polymer units, the organic zinc salt and long chain polyphosphates being mixed in amounts that provide a phosphorus to zinc mole ratio of 15:1 to about 55:1. Further provided is a method of making this soluble zinc polyphosphate.

8 Claims, No Drawings

(56) References Cited

FOREIGN PATENT DOCUMENTS

| WO | 2013/013903 | | 1/2013 |
| WO | WO 2013/013902 | ‡ | 1/2013 |
| WO | WO 2013/013903 | ‡ | 1/2013 |
| WO | 2014/098814 | | 6/2014 |
| WO | 2016/105433 | | 6/2016 |

\* cited by examiner
‡ imported from a related application

ZINC PHOSPHATE COMPLEX

CROSS REFERENCE TO RELATED APPLICATIONS

This application is a continuation of U.S. application Ser. No. 15/539,275, filed Jun. 23, 2017, which is a National Phase Application filed under 35 U.S.C. § 371 of International Application No. PCT/US2014/072421, filed on Dec. 26, 2014, the contents of each of which are incorporated herein by reference.

BACKGROUND

The present disclosure is directed to a soluble zinc polyphosphate complex for use in personal care compositions and methods of making the complex.

Zinc compounds are often used in oral care and personal care compositions. Many Zinc compounds possess hydrolysis chemistry and bacteria inhibiting qualities that render them suitable for oral care products. For instance, zinc is considered an anti-plaque agent. Compounds such as zinc citrate and zinc oxide have been added to toothpaste to prevent plaque buildup. Zinc salts can have other functions related to the body that make them desirable as active ingredients in other personal care products. For example, Zinc citrate as a trihydrate, $Zn_3(C_6H_5O_7)_2.3H_2O$, which is a white odorless powder that is only slightly soluble in water, serves as an important antioxidant nutrient and is vital for protein synthesis, blood stability, normal tissue function and wound healing to name a few common uses by the body.

Polyphosphates are known in the art for use as, for example, chelants, in oral care compositions. In addition, polyphosphates such as diphosphate (also known as pyrophosphate) and triphosphate are known for use as anions in antiperspirants, as taught in WO 2013/013903, published on Jan. 31, 2013. Longer chain linear polyphosphates (more than 3 phosphate units) are susceptible to hydrolysis in aqueous compositions. Upon hydrolysis they are known to form orthophosphates which form insoluble zinc complexes.

Dentinal hypersensitivity (i.e. sensitivity) is a painful condition resulting from the movement of liquid in exposed dentin tubules from external stimuli such as pressure and temperature. One strategy to reduce and/or eliminate the pain resulting from exposed dentin tubules is to form insoluble precipitates in the tubules in order to physically plug the tubules. For instance, Stannous salts have been shown to treat dentinal hypersensitivity by depositing into tubules from neat solutions and from simple formulations, as described in U.S. Patent Application Publication No. 2009/0136432, the disclosure of which is hereby incorporated by reference in its entirety.

Antiperspirant substances often employ aluminum containing actives. These substances reduce the flow of sweat by forming a plug in the sweat duct. However, due to consumer concern about aluminum based antiperspirant products, Aluminum free antiperspirant actives are in demand.

The discovery of a novel zinc complex that can be used to treat dentinal hypersensitivity and/or that can act as an antiperspirant active would be a welcome addition to the art. In addition, it would be desirable to manipulate zinc salt structures in efforts to enhance efficacy and extend the applications of these compounds in oral care and personal care products.

BRIEF SUMMARY

An embodiment of the present disclosure is directed to a soluble zinc polyphosphate complex made by combining ingredients wherein the ingredients comprise: an organic zinc salt; a plurality of long chain polyphosphates having 6 or more phosphate polymer units; and wherein the organic zinc salt and long chain polyphosphates are mixed in amounts that provide a phosphorus to zinc mole ratio of 15:1 to about 55:1.

In another embodiment, the present disclosure is directed to a method of making zinc polyphosphate, the method comprising: combining organic zinc salt; a plurality of long chain polyphosphates having 6 or more phosphate polymer units; and a solvent, the relative amount of organic zinc salt and long chain polyphosphates providing a phosphorus to zinc mole ratio of at least 6:1.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

An embodiment of the present disclosure is directed to a soluble zinc polyphosphate complex. The complex is made by combining ingredients comprising an organic zinc salt, a plurality of long chain polyphosphates having 6 or more phosphate polymer units and an aqueous solvent. The relative amount of organic zinc salt and long chain polyphosphates provides a phosphorus to zinc mole ratio of at least 6:1, such as about 15:1 to about 25:1.

In certain embodiments, the zinc polyphosphate complex has the property of reduced solubility in water at a first condition of 37° C. and a pH of about 7.4 in the presence of 1% by weight Bovine Serum Albumin protein when compared with a second condition of 25° C. and a pH of 5.4 in the absence of protein. The reduction in solubility is sufficient to allow a desired amount of the soluble zinc polyphosphate complex in a saturated solution at the second condition to precipitate from the saturated solution at the first condition.

Any suitable organic zinc ion source can be used to form the zinc complexes of the present disclosure. Examples of suitable organic zinc salts include zinc lactate, zinc citrate, zinc acetate, zinc gluconate, zinc malate, zinc tartrate and combinations thereof. Any of the organic zinc salts may or may not be in a hydrate form. For example, zinc citrate can be in a tryhydrated form (e.g., $Zn_3(C_6H_5O_7)_2 \cdot 3H_2O$). Thus use of organic zinc precursors results in an organic ligand being present in the resulting complex.

Any polyphosphates having 6 or more phosphate polymer units can be employed to form the zinc complexes of the present disclosure. In an embodiment, long chain polyphosphate having about 6 to about 50 phosphate polymer units, such as 6 to about 30 phosphate polymer units, can be used. An example of a long chain polyphosphate is sodium hexametaphosphate ("SHMP").

The phosphorus to zinc mole ratio can be any mole ratio of at least 6:1 that results in a soluble complex at the desired pH in an aqueous solution. In an embodiment, the phosphorus to zinc mole ratio ranges from about 10:1 to about 55:1, such as about 12:1 to about 40:1, or about 15:1 to about 25:1, about 18:1 to about 23:1, or about 20:1 to about 23:1.

The amount of zinc ion source to phosphate polymer reactant employed will vary depending on the desired phosphorus to zinc mole ratio and the particular reactants used. For example, a mole ratio range of about 15:1 to about 25:1 P to Zn mole ratio corresponds to about 5.5:1 to about 9.2 to 1 weight ratio of SHMP:ZnLac while having about a 2.5% w/w ZnLac concentration.

In an embodiment, the resulting zinc polyphosphate complex has an average of 15 or more P atoms. For example, the zinc polyphosphate complex can have an average of about 18 to about 25 P atoms, such as about 20 to 23 P atoms. In an embodiment, zinc polyphosphate complex formed in the composition has an average of about 1 zinc atom.

In an embodiment, the zinc polyphosphate complex has a property of becoming insoluble in aqueous solution at a pH ranging from 5.5 or above, such as above 7 to about 7.5 or higher, depending on the particular organic salt used to form the complex. The zinc polyphosphate complex can also have the property of being insoluble at a pH below 7 in aqueous solution in the presence of proteins, such as salivary proteins or skin proteins. The protein can be introduced during use, for example from the saliva, skin, or perspiration of a user. The amount of protein will vary depending on the conditions of use and can be any suitable amount that aids in triggering precipitation, such as, for example, about 0.1% by weight or more, or about 0.5% by weight or more, such as about 1% by weight.

When used in an oral care product, the soluble zinc and polyphosphate complexes of the present disclosure can remain soluble in composition until introduced into the oral cavity of a patient, at which point the complexes precipitate on biomaterial surfaces such as in dentinal tubules. For example, the soluble zinc polyphosphate complex can diffuse into dentinal tubules and precipitate, to thereby physically occlude the dentinal tubules and prevent dentinal hypersensitivity. In addition, in the presence of protein the zinc precipitate can have relatively strong acid resistance. Such protein can come, for example, from the saliva of a user, or can be added to the composition. Based on the results of the data, the new zinc complex is a potential candidate for, among other things, toothpastes for dentinal hypersensitivity relief.

Thus, the aqueous zinc polyphosphate complexes of the present disclosure can have one or more of the following advantages: the ability to remain soluble at pH below 7, such as below 5.5, the ability to precipitate at a pH above 5.5, such as above 7, the ability to occlude dentin tubules and relieve or eliminate dentinal hypersensitivity; the ability to form precipitates that remain insoluble at a pH below 7 in the presence of salivary proteins; the ability to in situ generate a precipitate upon interaction with saliva to effectively deliver zinc to the oral surface and provide dentin sensitivity relief, antimicrobial function, or any other benefit that may become apparent; the ability to in situ generate a precipitate upon interaction with skin proteins; or the ability to provide antimicrobial and/or anti-inflammatory effects when applied in a personal care product, such as deodorants or antiperspirants. Thus, this complex has high potential in the oral care and personal care fields.

The present disclosure is also directed to a method of making a soluble zinc polyphosphate complex. The method comprises combining organic zinc salt; a plurality of long chain polyphosphates having 4 or more phosphate polymer units; and an aqueous solvent. As discussed above, the relative amount of organic zinc salt and long chain polyphosphates provides a phosphorus to zinc mole ratio of at least 6:1. The ingredients can be mixed in any suitable order and using any suitable mixing technique with or without heating, so long as the method results in the formation of the desired soluble zinc polyphosphate complex.

In certain embodiments, the solvent used in the method is at least one solvent chosen from water, glycerin, diglycerol (glycerol-2), triglycerol (glycerol-3), quadraglycerol (glycerol-4), sorbitol, and polyethylene glycol having a weight average molecular weight less than 10,000. In one embodiment, the solvent is water. In one embodiment, the amount of solvent is 40 to 90 weight % based on a total weight of organic zinc salt, polyphosphate, and solvent. In other embodiments, the amount of solvent is 70 to 90 weight %, 75 to 85 weight %, or about 80 weight %.

Oral Care Compositions

The present disclosure is also directed to an oral care composition. The composition comprises a soluble zinc polyphosphate complex made by combining ingredients comprising an organic zinc salt, a plurality of long chain polyphosphates having 6 or more phosphate polymer units, and an aqueous solvent. The relative amount of organic zinc salt and long chain polyphosphates provides a phosphorus to zinc mole ratio of at least 6:1, such as at least 10:1, at least 12:1, at least 15:1, or at least 18:1, such as about 20:1; and wherein the zinc polyphosphate complex has increased solubility at a pH below 7.

The target amount of zinc to precipitate in the oral care composition can be any amount that will reduce dentinal hypersensitivity to a desired degree. In an embodiment, the amount is about 0.1 or more, such as about 0.1 to about 0.5, or about 0.3 to about 0.4. Suitable amounts of soluble zinc complex can be provided in the oral composition to achieve the desired target precipitate during use.

The oral compositions may be provided in an orally acceptable carrier or vehicle. The carrier can be a liquid, semi-solid, or solid phase, in the form of a mouth rinse or mouth wash, dentifrice (including toothpastes, toothpowders, and prophylaxis pastes), confectionaries (including lozenges and gum), medicament, film, or any other form known to one of skill in the art. Selection of specific carrier components is dependent on the desired product form.

In various embodiments, the oral composition has an orally acceptable vehicle that has a pH of about 6 to 10, or about 7 to 9. Certain components serve to raise the pH of the oral composition. Such compounds include conventional buffers and salts, as well as chemicals such as the anionic linear polycarboxylates (described above) and polyacrylates such as those available from B.F. Goodrich of Cleveland, Ohio sold under the trade name CARBOPOL® have been observed to raise pH when present in oral compositions.

Conventional ingredients can be used to form the carriers listed above. The oral compositions may include other materials in addition to those components previously described, including for example, surface active agents, such as surfactants, emulsifiers, and foam modulators, viscosity modifiers and thickeners, humectants, diluents, additional pH modifying agents, emollients, moisturizers, mouth feel agents, sweetening agents, flavor agents, colorants, preservatives, solvents, such as water and combinations thereof. Any given material may serve multiple purposes within two or more of such categories of materials. Preferably, such carrier materials are selected for compatibility and stability with all of the constituents of the active ingredient.

Useful surface active agents are known in the art, such as those disclosed in U.S. Pat. No. 4,894,220, the disclosure of which is incorporated herein by reference in its entirety. Surface active agents can function as surfactants, emulsifiers foam modulators, and/or active ingredient dispersion agents.

Suitable surface active agents are those that are reasonably stable and foam throughout a wide pH range. These compounds are known in the art, and include non-soap anionic (e.g., sodium lauryl sulfate (SLS), N-myristoyl, and N-palmitoyl sarcosine), nonionic (e.g., Polysorbate 20 (polyoxyethylene 20 sorbitan monolaurate, TWEEN® 20) and Polysorbate 80 (polyoxyethylene 20 sorbitan monooleate, TWEEN® 80), Poloxamer 407, available under the trade name PLURONIC® F127 from BASF Corporation), cationic, zwitterionic (e.g., cocoamidopropyl betaine and lauramido propyl betaine), and amphoteric organic synthetic detergents. In various embodiments, one or more surface active agents are present in the oral composition in the range of about 0.001% to about 5%, or about 0.5% to about 2.5%. In embodiments where the oral composition comprises an active ingredient comprising lipophilic active compound(s), the amount of surface active agent can be increased to enable sufficient emulsification of the active ingredients within the carrier of the oral composition. The carrier can be, for example, an aqueous carrier.

In an embodiment, the zinc salts of the present disclosure can be used in translucent aqueous formulations, such as mouthrinse. In embodiments where the oral composition is in the form of a mouthrinse, an exemplary carrier is substantially liquid. The term "mouthrinse" includes mouthwashes, sprays and the like. In such a preparation the orally acceptable carrier typically has an aqueous phase comprising either water, or a water and alcohol mixture. Further, in various embodiments, the oral carrier can comprise, for example, a humectant, surfactant, and a pH buffering agent.

The oral composition may optionally comprise a flavoring agent. Exemplary flavoring substances are known to a skilled artisan, and may be present in certain embodiments at a concentration of about 0.05% by weight to about 5% by weight.

In embodiments where an oral composition is in the form of a confectionary, an exemplary carrier may be substantially solid or semi-solid. Confectionary carriers are known in the art. For a lozenge, the carrier can comprise, for example, a lozenge base material (for example, comprising a non-cariogenic polyol and/or starch/sugar derivative), an emulsifier, a lubricant, a flavoring agent, a thickener, and optionally a coating material. Chewing gum carriers generally have a chewing gum base, one or more plasticizing agents, a sweetening agent, and a flavoring agent.

In embodiments where an oral composition is in the form of a film, an exemplary carrier is substantially solid or semi-solid. Such film carriers can comprise, for example, a water soluble or dispersible film forming agent, such as a hydrophilic polymer. Optionally, the film carrier may also comprise hydrophobic film forming polymers, either as a removable backing layer, or mixed with a hydrophilic film forming polymer. Film carriers optionally comprise plasticizers, surface active agents, fillers, bulking agents, and viscosity modifying agents.

In embodiments where an oral composition is in the form of a dentifrice, an exemplary carrier is substantially semi-solid or a solid. Dentifrices can comprise, for example, surface active agents, humectants, viscosity modifying agents and/or thickeners, abrasives, solvents, such as water, flavoring agents, and sweetening agents.

In embodiments an oral composition is in the form of a medicament, such as a non-abrasive gel or ointment that can be applied to the gingival sulcus or margin and can be used in conjunction with wound dressings, gauze, films, and the like. Such gels may include both aqueous and non-aqueous gels. Aqueous gels generally comprise a polymer base, a thickener, a humectant, a flavoring agent, a sweetening agent, and a solvent, typically including water.

In various embodiments, the compositions and methods of the present disclosure promote oral health in an oral cavity and treat plaque on an oral surface of a mammalian subject. In one embodiment, a method of providing one or more oral health benefits to an oral cavity of a mammalian subject entails preparing an oral composition as described herein, where an active ingredient comprises any of the soluble zinc polyphosphate complexes disclosed herein. The prepared oral composition is contacted with an oral surface within an oral cavity. In addition to treating dentinal hypersensitivity, compositions of the present disclosure containing the active ingredient may provide multiple oral health and body health benefits, such as anti-gingivitis, anti-periodontitis, anti-caries, anti-tartar, anti-microbial, anti-inflammatory, analgesic, anti-aging, and breath freshening. Several of these benefits can be advantages in personal care products other than oral compositions. Such personal care products are described in greater detail below.

Thus, any of the various embodiments of the oral care composition described above are contacted with or applied regularly to an oral surface, such as at least one time a day, or on multiple days in a week.

The oral composition of the present invention can be made by any of the methods known in the art for combining ingredients to make oral care compositions. Methods for making the oral compositions comprising a soluble zinc polyphosphate complex, as described herein, are well within the ordinary skill of the art.

Personal Care Compositions

The compositions of the present disclosure can be used in personal care composition. Examples of such compositions include, but are not limited to, antiperspirants, deodorants, body washes, shower gels, bar soaps, shampoo, hair conditioners and cosmetics.

For antiperspirant and/or deodorant compositions, the carrier can be any carrier that is used for antiperspirants and/or deodorants. The carrier can be in the form of a stick, a gel, a roll-on or an aerosol. For stick formulations, the carrier may include oils and/or silicones and gelling agents. An example of a formulation can be found in US2011/0076309A1, which is incorporated herein by reference in its entirety.

In an embodiment, the personal care compositions, such as antiperspirants and/or deodorants, include a soluble zinc polyphosphate complex made by combining ingredients comprising an organic zinc salt, a plurality of long chain polyphosphates having 6 or more phosphate polymer units, and an aqueous solvent. The relative amount of organic zinc salt and long chain polyphosphates provides a phosphorus to zinc mole ratio is at least 6:1, such as at least 10:1, at least 12:1, at least 15:1, or at least 18:1, such as about 20:1; and can be any of the other phosphorus to zinc mole ratios taught herein for the soluble zinc polyphosphate complex.

The amount of zinc in a personal care composition can be any suitable effective amount. Suitable amounts of zinc can range, for example, from about 0.2% by weight or more, such as about 0.5% to about 10% by weight, relative to the total weight of the composition.

As described above, the zinc polyphosphate complex has the property of reduced solubility in water at certain temperature and pH conditions, but is soluble at other conditions. In an embodiment, the formulation can be formulated without added protein, such as BSA. The protein desired to trigger precipitation can be provided by the sweat of the user after application of the product.

In an embodiment, the zinc polyphosphate complex can have reduced solubility at, for example, a condition of 37° C. and a pH of about 7.4 in the presence of 1% by weight Bovine Serum Albumin protein when compared with a second condition of 25° C. and a pH of 5.4 in the absence of protein. The reduction in solubility can be sufficient to allow a desired amount of the soluble zinc polyphosphate complex in a saturated solution at the second condition to precipitate from the saturated solution at the first condition, as described above.

In an embodiment, the protein can also be used to enhance the efficacy of other antiperspirant salts comprising a polyvalent cation, for example antiperspirant complexes of (i) aluminum and optionally zirconium, (ii) chlorohydrate, and (iii) optionally an amino acid and/or ammonium acid, for example glycine and/or trimethylglycine, e.g., aluminum zirconium tetrachlorohydrex glycine. In an embodiment, these other antiperspirant salts can be added to the formulations of the present disclosure in addition to the zinc polyphosphate complex antiperspirant. In an alternative embodiment, the formulation includes only very small amounts or is entirely or substantially free of the above aluminum or zirconium antiperspirant active complexes. For example, the formulations can include less than 2 wt %, or less than 0.5 wt %, or less than 0.1 wt. %, or less than 0.01 wt. %, or less than 0.001 wt. % or less than 0.0001 wt. % aluminum or zirconium, relative to the total weight of the formulation.

The present disclosure thus provides antiperspirant products comprising a zinc polyphosphate complex antiperspirant active, e.g., any of the zinc polyphosphate complexes discussed herein, as well as methods of making and using such products. The disclosure further provides methods of reducing sweat and/or odor comprising applying the composition to skin, and methods of killing bacteria comprising contacting the bacteria with the composition.

Optional ingredients that can be included in an antiperspirant and/or deodorant formulations of the present disclosure include solvents; water-soluble alcohols such as $C_{2-8}$ alcohols including ethanol; glycols including propylene glycol, dipropylene glycol, tripropylene glycol and mixtures thereof; glycerides including mono-, di- and triglycerides; medium to long chain organic acids, alcohols and esters; surfactants including emulsifying and dispersing agents; amino acids including glycine; structurants including thickeners and gelling agents, for example polymers, silicates and silicon dioxide; emollients; fragrances; and colorants including dyes and pigments. If desired, an antiperspirant and/or deodorant agent additional to the soluble zinc polyphosphate complex can be included, for example an odor reducing agent such as a sulfur precipitating agent, e.g., copper gluconate, zinc gluconate, zinc citrate, etc.

The antiperspirant compositions can be formulated into topical antiperspirant and/or deodorant formulations suitable for application to skin, illustratively a stick, a gel, a cream, a roll-on, a soft solid, a powder, a liquid, an emulsion, a suspension, a dispersion or a spray. The composition can comprise a single phase or can be a multi-phase system, for example a system comprising a polar phase and an oil phase, optionally in the form of a stable emulsion. The composition can be liquid, semi-solid or solid. The antiperspirant and/or deodorant formulation can be provided in any suitable container such as an aerosol can, tube or container with a porous cap, roll-on container, bottle, container with an open end, etc.

The compositions can be used in a method to reduce sweating by applying the composition to skin. In certain embodiments, the application is to axilla. Also, the compositions can be used to kill bacteria by contacting bacteria with the composition comprising the zinc complexes of the present disclosure. In embodiments, other additives for killing bacteria can also be employed in the compositions of the present disclosure. Various suitable additional antimicrobial additives are known in the art.

Thus the present disclosure provides (i) a method for controlling perspiration comprising applying to skin an antiperspirant effective amount of a formulation of any embodiment embraced or specifically described herein; and (ii) a method for controlling odor from perspiration comprises applying to skin a deodorant effective amount of a formulation of any embodiment embraced or specifically described herein.

The present disclosure is further illustrated through the following non-limiting example(s).

EXAMPLES

Examples 1 to 6

Zinc lactate and sodium hexametaphosphate (SHMP) were mixed to target mol ratios and then diluted to a total of 10 g solution with DI water. Reagents were weighed with an electronic scale having an ±0.0001 g accuracy. Target mole ratios for Examples 1 to 6 are as shown in Table 1 below. The mixtures were sonicated and the different behaviors of zinc phosphate at the different mole ratios were recorded. After being sonicated, samples of the example formulations 1 to 6 were aged in an oven at 50° C. for 17 hours. Other samples of the example formulations 1 to 6 were aged at room temperature for 6 days. The results of these tests are shown in Table 1.

TABLE 1

| Example | ZnLac (g) | SHMP (g) | P:Zn Mole Ratio | Total (g) | Observation After Sonicated | After Oven | After 6 days RT |
|---|---|---|---|---|---|---|---|
| 1 | 0.25 | 0.092 | 1 | 10.012 | Cloudy, precip. | Precip | Precip |
| 2 | 0.25 | 0.46 | 5 | 10.005 | Cloudy, precip. | Precip | Precip |

TABLE 1-continued

| Example | ZnLac (g) | SHMP (g) | P:Zn Mole Ratio | Total (g) | Observation After Sonicated | After Oven | After 6 days RT |
|---|---|---|---|---|---|---|---|
| 3 | 0.25 | 0.92 | 10 | 10.62 | Clear | Precip | Precip |
| 4 | 0.25 | 1.84 | 20 | 10.129 | Clear | Clear | Clear |
| 5 | 0.25 | 3.68 | 40 | 10.325 | Clear | Clear | Precip |
| 6 | 0.25 | 5.52 | 60 | 10.006 | Amorphous precip. | Precip | Precip |

After sonication, Examples 3, 4 and 5 were clear, indicating that a soluble zinc polyphosphate complex had formed in each of those samples. Samples 4 and 5 remained clear after aging in the oven at 50° C. It was found that after a week, only the formulation of Example 4 stayed soluble while all the other samples precipitated.

Based on these results, it was determined that zinc complex made with zinc lactate and sodium hexametaphosphate became soluble, resulting in the solution becoming clear, when combined at mole ratio of P:Zn of approximately 20:1 (reagent mass ratio of 2.5% w/w zinc salt per 18.41% w/w SHMP) or approximately 21:1 (reagent mass ratio SHMP:ZnL=8:1).

Because the average chain length of the zinc polyphosphate complex is 23P and mole ratio of P:Zn is about 20:1 or 21:1, it is predicted that for this soluble zinc Phosphate species, 1 zinc is bonded to each phosphate chain on average.]

Examples 7 and 8

Samples of the formulation of Example 4 were mixed with protein (1% Bovine serum albumin ("BSA")). One sample (Example 7) was heated to 37° C. and aged overnight. Another sample (Example 8) was aged at room temperature overnight. Both formulations were then further aged for a week at room temperature.

The samples appeared clear prior to aging. Upon aging overnight, white precipitates formed in both the formulations of Examples 7 and 8. Additional precipitates appeared to form in both samples after aging for a week. The Example 7 formulation showed more precipitates than the Example 8 formulation both after aging overnight and after a week.

Example 9

0.6247 grams of zinc lactate and 4.603 grams of SHMP were added to an aqueous solution to form 25.035 total grams of solution. Two samples, a 5.7 gram sample (Example 9) and a 5.12 gram sample (control sample) of the solution were added to glass containers. The pH of the Example 9 solution was carefully adjusted from a starting pH of 4.77 to a pH 7.56 by adding sodium hydroxide, at which point a precipitate formed. The pH of the solution was then lowered by carefully adding hydrochloric acid until the precipitates dissolved completely at a pH of 7.03. This data indicates that the aqueous soluble zinc lactate polyphosphate complex will generate white zinc precipitates when pH is raised to above 7.

In order to determine if the Example 9 solution would precipitate at oral conditions (pH 7.4 and 37° C.) the pH of the solution was further decreased from 7.03 by adding hydrochloric acid until a pH of 6.1 was reached, and the solution was then aged overnight at a mouth condition (37° C.). Precipitates were formed and settled on the bottom of the glass container after aging. This provides strong evidence that the zinc lactate and SHMP complex is a potential active for dentinal hypersensitivity relief.

Based on the above data, it is believed that the soluble zinc phosphate mixture can potentially be used in dentinal tubules mitigation toothpaste or other oral compositions used for treating dentinal hypersensitivity. At a certain molar ratio (approximately 20P:1Zn), soluble Zinc solution can be obtained when Zinc lactate is mixed with Sodium Hexametaphosphate. While not wishing to be bound by theory, it is theorized that soluble Zinc polyphosphate solution indicates that a complex is being formed between Zn cations and phosphate anions. When this soluble solution is mixed with BSA protein, it quickly starts to precipitate and will be able to block the tubules. In addition, $Zn^{2+}$ will hydrolyze to amorphous zinc hydroxide to physically block the tubules.

Example 10

Examples 10 to 20 below were freshly prepared using zinc citrate trihydrate and sodium hexametaphosphate ("SHMP") (0.009736 mol Phosphorus per gram of SHMP; 69.1% $P_2O_5$ per gram of SHMP) at the P/ZN mole ratios shown in Table 2. Reagents were used as received by the manufacturer. Samples were weighed using a laboratory scale (±0.0001 g) and then mixed in scintillation vials.

TABLE 2

Solution Preparation at Various Ratios

| Example | P/Zn Mole Ratio | Weight (g) | Actual Percent in solution | Appearance | pH |
|---|---|---|---|---|---|
| 10 | 2 | 0.2031 g ZnCit<br>0.2062 g SHMP powder<br>9.7629 g water | 2.00% ZnCit<br>2.03% SHMP<br>95.97% water | Solution appears turbid | |
| 11 | 3 | 0.2038 g ZnCit<br>0.3081 g SHMP powder<br>9.6582 g water | 2.00% ZnCit<br>3.03% SHMP<br>94.97% water | Solution appears turbid | |
| 12 | 4 | 0.2040 g ZnCit<br>0.4112 SHMP powder<br>9.5574 g water | 2.01% ZnCit<br>4.04% SHMP<br>93.95% water | Solution is clear but appears turbid after 1 day at RT | |
| 13 | 5 | 0.2032 g ZnCit<br>0.9990 g 50% SHMP solution<br>8.9635 g water | 2.00% ZnCit<br>4.91% SHMP<br>93.09% water | Solution is clear for 1 week | 5.13 |
| 14 | 10 | 0.2038 g ZnCit<br>2.0402 g 50% SHMP solution<br>8.0710 g water | 1.98% ZnCit<br>9.89% SHMP<br>88.13% water | Solution remains clear | 5.08 |

TABLE 2-continued

Solution Preparation at Various Ratios

| Example | P/Zn Mole Ratio | Weight (g) | Actual Percent in solution | Appearance | pH |
|---|---|---|---|---|---|
| 15 | 21 | 0.2031 g ZnCit<br>2.1571 g SHMP powder<br>7.8085 g water | 2.00% ZnCit<br>21.21% SHMP<br>76.79% water | Solution remains clear | 4.99 |
| 16 | 30 | 0.2036 g ZnCit<br>5.9915 g 50% SHMP solution<br>3.9696 g water | 2.00% ZnCit<br>29.47% SHMP<br>68.53% water | Solution remains clear | 4.78 |
| 17 | 50 | 0.2038 g ZnCit<br>10.2744 g 50% SHMP solution<br>0 g water | 1.94% ZnCit<br>49.03% SHMP<br>49.03% water | Solution remains clear | 4.68 |
| 18 | 55 | 0.2030 g ZnCit<br>5.6493 g SHMP powder<br>4.3134 g water | 2.00% ZnCit<br>55.57% SHMP<br>42.43% water | Solution appears turbid | |
| 19 | 60 | 0.2036 g ZnCit<br>6.1621 g SHMP powder<br>3.8045 g water | 2.00% ZnCit<br>60.59% SHMP<br>37.41% water | Solution appears turbid | |
| 20 | 70 | 0.2028 g ZnCit<br>7.1890 g SHMP powder<br>2.7770 g water | 1.99% ZnCit<br>70.70% SHMP<br>27.31% water | Solution appears turbid | |

As Table 2 shows, the P/Zn mole ratios spanning from above 4P/Zn to below 55P/Zn form a clear solution when mixed. It was concluded that a complex forms between the zinc citrate and SHMP.

Examples 21 to 26

Examples 21 to 26 of Table 3 below were freshly prepared using zinc citrate trihydrate and sodium hexametaphosphate ("SHMP") (0.009736 mol Phosphorus per gram of SHMP; 69.1% $P_2O_5$ per gram of SHMP) at the P/ZN mole ratios shown in Table 3. Reagents were used as received by the manufacturer. Samples were weighed using a laboratory scale (±0.0001 g) and then mixed in scintillation vials.

TABLE 3

Solution Preparation of Low P/Zn Ratio Solutions for Aging Study

| Example | P/Zn Mole Ratio | Weight (g) | Actual Percent in solution | pH |
|---|---|---|---|---|
| 21 | 20 | 0.2103 g ZnCit<br>2.0539 g SHMP powder<br>8.2067 g water | 2.01% ZnCit<br>19.62% SHMP<br>78.38% water | 5.16 |
| 22 | 15 | 0.2102 g ZnCit<br>1.6511 g SHMP powder<br>8.6046 g water | 2.01% ZnCit<br>15.78% SHMP<br>82.22% water | 5.22 |
| 23 | 10 | 0.2093 g ZnCit<br>1.02649 g SHMP<br>9.2328 g water | 2.00% ZnCit<br>9.80% SHMP<br>88.20% water | 5.24 |
| 24 | 8 | 0.2089 g ZnCit<br>0.8225 g SHMP<br>9.4387 g water | 2.00% ZnCit<br>7.85% SHMP<br>90.15% | 5.26 |
| 25 | 6 | 0.2096 g ZnCit<br>0.6165 g SHMP powder<br>9.6436 g water | 2.00% ZnCit<br>5.89% SHMP<br>92.11% water | 5.18 |
| 26 | 5 | 0.2096 g ZnCit<br>0.5140 g SHMP powder<br>9.7432 g water | 2.00% ZnCit<br>4.91% SHMP<br>93.09% water | 5.25 |

Examples 27 to 32—Aging Study

Two sets of samples for each of the solutions of Table 3 with a P/Zn mole ratio of 20, 15, 10, 8, 6, and 5 were taken. One set of samples was aged at room temperature (about 20° C.) for a week. The other set of samples was aged at 37° C. for a week. The solutions aged at room temperature and containing a mole ratio ranging from 20 P/Zn to 6 P/Zn were stable at room temperature and remained clear throughout the aging period. The solution with a mole ratio of 5 P/Zn became turbid at room temperature and the precipitate settled to the bottom of the flask. For the solutions aged at 37° C., in the range of 20 P/Zn to 5 P/Zn mole ratio solutions, only the 20P/Zn mole ratio solution remained stable (not turbid, without visible precipitate).

Examples 33 to 38—Aging Studing with BSA

Examples 33 to 38 of Table 4 below were freshly prepared using zinc citrate trihydrate and sodium hexametaphosphate ("SHMP") (0.009736 mol Phosphorus per gram of SHMP; 69.1% $P_2O_5$ per gram of SHMP) at the P/ZN mole ratios shown in Table 3. The pH was adjusted using sodium hydroxide and/or hydrochloric acid. 1% by weight BSA protein was added to each sample. Reagents were used as received by the manufacturer. Samples were weighed using a laboratory scale (±0.0001 g) and then mixed in scintillation vials. A control sample of 1% BSA solution of DI water was also prepared.

TABLE 4

Solution Preparation of 1% BSA Solutions

| Example | Sample | Amount of BSA (g) | Amount of Total Solution |
|---|---|---|---|
| 33 | 1% BSA in 1Zn:20P solution | 0.0200 g | 2.0371 g |
| 34 | 1% BSA in 1Zn:15P solution | 0.0195 g | 2.0211 g |
| 35 | 1% BSA in 1Zn:10P solution | 0.0209 g | 2.0050 g |
| 36 | 1% BSA in 1Zn:8P solution | 0.0199 g | 1.9997 g |
| 37 | 1% BSA in 1Zn:6P solution | 0.0194 g | 2.0021 g |
| 38 | 1% BSA in 1Zn:5P solution | 0.0200 g | 1.9976 g |
| Control Sample | 1% BSA in DI water | 0.0207 g | 2.0031 g |

The solutions of Table 4, having a P/Zn mole ratio of 20, 15, 10, 8, 6, and 5 and containing 1% BSA were aged at 37° C. for two days and were compared to the control solution of 1% BSA in DI water. After aging, the control sample having a 1% BSA solution of DI water did not form a precipitate and remained clear. All of the zinc citrate and SHMP solutions containing 1% BSA formed a precipitate.

Examples 39 to 41—Solution Preparation and Aging of 10% Saliva Solutions

Examples 39 to 42 of Table 5 below were freshly prepared using zinc citrate trihydrate and sodium hexametaphosphate ("SHMP") (0.009736 mol Phosphorus per gram of SHMP; 69.1% $P_2O_5$ per gram of SHMP) at the P/ZN mole ratios shown in Table 3. 10% by weight saliva was added. The amount of BSA protein shown in Table 5 was added to each sample. Reagents were used as received by the manufacturer. Samples were weighed using a laboratory scale (±0.0001 g) and then mixed in scintillation vials. A control sample of 1% BSA solution of DI water was also prepared.

TABLE 5

| Example | Sample | Amount of BSA (g) | Amount of Total Solution |
|---|---|---|---|
| 39 | 10% Saliva in 1Zn:20P solution | 0.2039 g | 2.0037 g |
| 40 | 10% Saliva in 1Zn:10P solution | 0.2014 g | 2.0119 g |
| 41 | 10% Saliva in 1Zn:6P solution | 0.2130 g | 2.0053 g |
| 42 | Control: 10% Saliva in DI water | 0.2065 g | 2.0031 g |

The solutions with a P/Zn mole ratio of 20, 10 and 6 containing 10% saliva from Table 5 were aged at 50° C. for two days and were compared to the control solution of 10% saliva in DI water. The ZnCit+SHMP with saliva solutions at 50° C. become turbid (precipitates formed) compared to the 10% saliva control solution at 50° C., which remained relatively clear.

Example 42

A zinc citrate trihydrate and sodium hexametaphosphate ("SHMP") (0.009736 mol Phosphorus per gram of SHMP; 69.1% $P_2O_5$ per gram of SHMP) at the P/ZN mole ratio of 20 was prepared. The initial pH of the 20P/1Zn ratio solution was measured to be 4.95. The pH was then raised in small increments using NaOH. The solution remained clear at every pH increment below 9.67. At pH=9.67 the solution became turbid. The pH of the solution was then lowered using HCl. At pH=8.99, the solution was still turbid but noticeably less turbid than at 9.67. At pH=8.56, the solution appeared clear again.

Example 43

A zinc citrate trihydrate and sodium hexametaphosphate ("SHMP") (0.009736 mol Phosphorus per gram of SHMP; 69.1% $P_2O_5$ per gram of SHMP) at the P/ZN mole ratio of 15 was prepared. The initial pH of the 15P/1Zn mole ratio solution was measured to be 4.93. The pH was then raised in small increments using NaOH. The solution remained clear at every pH increment below 9.46. At pH=9.46 the solution appeared slightly turbid and at pH=9.64, the solution was even more turbid. Upon lowering this solution using HCl, at pH 8.74, the solution appeared clear once again.

Example 44

Because a SHMP+ZnCit solution in a 1Zn:20P mole ratio gave a clear solution when the zinc citrate concentration in the final solution was 2% by weight, the same ratio was used in the preparation of higher concentrations of zinc citrate in zinc citrate+SHMP solutions, as shown in Tables 6 and 7.

TABLE 6

3.0% Zinc Citrate

| | Mass (g) | Actual Percent (%) | pH Upon Preparation |
|---|---|---|---|
| SHMP | 2.0546 | 29.38% | 4.87 |
| Water | 4.7286 | 67.62% | |
| ZnCit | 0.2094 | 3.00% | |

TABLE 7

2.5% Zinc Citrate

| | Mass (g) | Actual Percent (%) | pH Upon Preparation |
|---|---|---|---|
| SHMP | 2.0548 | 24.53% | 4.92 |
| Water | 6.1149 | 72.98% | |
| ZnCit | 0.2085 | 2.49% | |

Both the 2.5% and 3.0% by weight solutions of Tables 6 and 7 appeared turbid after aging at room temperature (about 20° C.) for one day. Since 2% Zinc Citrate gives a clear solution and other solutions with greater concentrations of zinc citrate appear turbid. This data suggests that the highest amount of Zinc Citrate that can be added to the SHMP solution is between 2% to 2.5% in the final solution if it is desired to avoid precipitation of the complex.

The novel complexes formed from insoluble Zinc Citrate trihydrate and poly phosphate (SHMP), as described in the above examples, present as clear solutions at various P/Zn mole ratios ranging from above 5P/Zn to below 55P/Zn. After aging for a week at room temperature, the solutions that remained stable ranged between 6 P/Zn and 20 P/Zn. Upon aging the various ratios at 37° C. for a week, the 20 P/Zn mole ratio solution remained completely clear. This indicates that at higher temperatures (e.g., biological temperatures, such as human body temperature), complexes of the present disclosure having a mole ratio of about 20P/1Zn can remain soluble. Further adjustment of the pH of such a solution, as well as that of the 15P/1Zn ratio solution, indicates that the solution remains clear even at a high pH of around 9.6. The stability of the solution at a high pH renders it compatible with formulations possessing a neutral or high pH. The above data showed that the highest amount of zinc citrate that can be loaded into the 20P/Zn mole ratio solution prior to precipitation ranges between 2%-2.5% of the trihydrate powder at a pH of approximately 4.9 and room temperature.

It was also found that when zinc citrate is mixed with SHMP in a ratio greater than 1Zn:6P and less than 1Zn:55P, the resulting solution appears clear with a pH of 5±0.2. Furthermore, it is reported that upon addition of BSA and saliva, separately, the zinc citrate-phosphate complex forms a precipitate. Upon addition of saliva to the solutions at 50° C. ranging from 6P/Zn to 20P/Zn, all of the solutions became turbid, indicating the formation of a precipitate upon interaction with saliva. Lowering the pH back produced a clear solution, once again.

Based on this data, it is believed that the soluble complexes of the present disclosure will allow delivery of precipitate to block dentin tubules and thereby provide sensitivity relief when used in oral compositions. Further, BSA in the above experiments simulates sweat proteins. Based on the data, it is believed that the complexes of the present disclosure can diffuse into sweat glands and precipitate in combination with protein to block the sweat ducts of a user, thereby preventing or reducing the amount of sweat from coming out skin when used as an active ingredient in antiperspirants. In essence, the solubility characteristics of the zinc complex allows it to readily diffuse into dentin tubules or sweat glands and precipitate, thereby blocking the tubules or glands. The solubility can also allow formulation into liquid products, such as mouthwash. Additionally, the soluble Zinc complex can potentially be used to make transparent products.

What is claimed is:

1. A soluble zinc polyphosphate complex made by combining ingredients wherein the ingredients comprise:
   an organic zinc salt comprising zinc citrate;
   sodium hexametaphosphate; and
   water;
   wherein the zinc citrate and sodium hexametaphosphate are mixed in amounts that provide a phosphorus to zinc mole ratio of 20:1; and
   wherein the zinc polyphosphate complex has the property of reduced solubility in water at a first condition of 37° C. and a pH of about 7.4 in the presence of 1% by weight Bovine Serum Albumin protein when compared with a second condition of 25° C. and a pH of 5.4 in the absence of protein, the reduction in solubility being sufficient to allow the soluble zinc polyphosphate complex in a saturated solution at the second condition to precipitate from the saturated solution at the first condition.

2. The complex of claim 1, wherein the zinc polyphosphate complex has an average of 18 or more P atoms.

3. The complex of claim 1, wherein the zinc polyphosphate complex has an average of about 20 to about 25 P atoms.

4. The complex of claim 1, wherein the zinc polyphosphate complex has an average of about 1 zinc atom.

5. A method of making the zinc polyphosphate complex according to claim 1, the method comprising:
   combining the zinc citrate; sodium hexametaphosphate; and water, the relative amount of zinc citrate and sodium hexametaphosphate providing a phosphorus to zinc mole ratio of 20:1; and wherein the zinc polyphosphate complex has the property of reduced solubility in water at a first condition of 37° C. and a pH of about 7.4 in the presence of 1% by weight Bovine Serum Albumin protein when compared with a second condition of 25° C. and a pH of 5.4 in the absence of protein, the reduction in solubility being sufficient to allow the soluble zinc polyphosphate complex in a saturated solution at the second condition to precipitate from the saturated solution at the first condition.

6. The method of claim 5, wherein the amount of water based on the total weight of zinc citrate, sodium hexametaphosphate, and water is 40 to 90 weight %.

7. The method of claim 5, wherein the amount of water based on the total weight of zinc citrate, sodium hexametaphosphate, and water is 70 to 90 weight %.

8. The method of claim 5, wherein the amount of water based on the total weight of zinc citrate, sodium hexametaphosphate, and water is 75 to 85 weight %.

* * * * *